(12) United States Patent
Nilakantan

(10) Patent No.: US 11,285,673 B2
(45) Date of Patent: Mar. 29, 2022

(54) MACHINE-LEARNING-BASED ADDITIVE MANUFACTURING USING MANUFACTURING DATA

(71) Applicant: Padmanabhan Nilakantan, Torrance, CA (US)

(72) Inventor: Padmanabhan Nilakantan, Torrance, CA (US)

(73) Assignee: NORTHROP GRUMMAN SYSTEMS CORPORATION, Falls Church, VA (US)

( * ) Notice: Subject to any disclaimer, the term of this patent is extended or adjusted under 35 U.S.C. 154(b) by 208 days.

(21) Appl. No.: 16/717,624

(22) Filed: Dec. 17, 2019

(65) Prior Publication Data

US 2021/0178697 A1 Jun. 17, 2021

(51) Int. Cl.
*G06F 19/00* (2018.01)
*B29C 64/393* (2017.01)
(Continued)

(52) U.S. Cl.
CPC ............ *B29C 64/393* (2017.08); *B33Y 10/00* (2014.12); *G05B 13/0265* (2013.01);
(Continued)

(58) Field of Classification Search
CPC .. G05B 19/4099; G05B 13/0265; G06N 3/08; G06N 20/00; G06F 40/284;
(Continued)

(56) References Cited

U.S. PATENT DOCUMENTS

2013/0080066 A1* 3/2013 Al-Dossary ............ G01V 1/306
702/11
2017/0312614 A1* 11/2017 Tran ......................... A61B 5/11
(Continued)

FOREIGN PATENT DOCUMENTS

EP 3422281 A1 1/2019
EP 3495904 A1 6/2019

OTHER PUBLICATIONS

International Search Report for Application No. PCT/US2020/054263 dated Dec. 8, 2020.
(Continued)

*Primary Examiner* — Tuan A Vu
(74) *Attorney, Agent, or Firm* — Tarolli, Sundheim, Covell & Tummino LLP

(57) ABSTRACT

Systems and methods for machine-learning-based additive manufacturing use a machine-learning model to process an input vector describing a new part transaction, thereby providing part optimization outputs and command initiation outputs to configure additive manufacturing of a new part. The machine-learning model is trained based on entries in a user experience database, each entry in the user experience database including data defining requirements for an additively manufactured part previously fabricated or attempted to be fabricated, specifications describing an additive manufacturing fabrication device, a selection of a raw material type fed to the fabrication device for fabrication of the additively manufactured part, a fabrication spatial orientation of the additively manufactured part within the fabrication device, a fabrication slicing resolution of the additively manufactured part, and a toolpath taken by the fabrication device in fabricating the additively manufactured part.

11 Claims, 12 Drawing Sheets

(51) Int. Cl.
*B33Y 10/00* (2015.01)
*G06N 20/00* (2019.01)
*H04L 9/06* (2006.01)
*G05B 13/02* (2006.01)
*G06F 40/284* (2020.01)
*G06F 40/117* (2020.01)
*G06N 3/08* (2006.01)
*B33Y 50/02* (2015.01)
*A61B 5/11* (2006.01)
*G06F 30/3312* (2020.01)
*G01V 1/30* (2006.01)

(52) U.S. Cl.
CPC .......... *G06F 40/117* (2020.01); *G06F 40/284* (2020.01); *G06N 3/08* (2013.01); *G06N 20/00* (2019.01); *H04L 9/0637* (2013.01); *A61B 5/11* (2013.01); *B33Y 50/02* (2014.12); *G01V 1/306* (2013.01); *G06F 30/3312* (2020.01); *H04L 2209/38* (2013.01)

(58) Field of Classification Search
CPC ...... G06F 30/3312; G06F 40/117; A61B 5/11; A61B 18/1485; G01V 1/306; B33Y 10/00; B33Y 50/02; H04L 2209/38; B29C 64/393
See application file for complete search history.

(56) References Cited

U.S. PATENT DOCUMENTS

| | | | |
|---|---|---|---|
| 2018/0341248 A1* | 11/2018 | Mehr | G06N 3/08 |
| 2019/0101896 A1* | 4/2019 | Cantrell | G05B 19/4099 |
| 2019/0228126 A1* | 7/2019 | Oh | G06F 30/3312 |
| 2019/0348041 A1* | 11/2019 | Celia | G06F 40/284 |
| 2020/0098195 A1* | 3/2020 | Jaiswal | G05B 13/0265 |
| 2020/0218858 A1* | 7/2020 | Sawyer | G06F 40/117 |
| 2020/0305967 A1* | 10/2020 | Getman | A61B 18/1485 |

OTHER PUBLICATIONS

Xinbo Qi et al: "Applying Neural-Network-Based Machine Learning to Additive Manufacturing: Current Applications, Challenges and future Perspectives", Engineering,, vol. 5, No. 4, Jul. 3, 2019 (Jul. 3, 2019), pp. 721-729, XP002796699, DOI: https://doi.org/10.1016/J.Eng.2019.04.012 Section 4.3; p. 726-p. 727.

Wang Rong-Ji et al: "Optimizing process parameters for selective laser sintering based on neural network and genetic algorithm", The International Journal of Advanced Manufacturing Technology, Springer, London vol. 42, No. 11-12, Jun. 1, 2009 (Jun. 1, 2009), pp. 1035-1042, XP002610275, ISSN: 0268-3768, DOI: 10.1007/S00170-008-1669-0 Retrieved from the Internet: URL: http://www.springerlink.com/content/w86x57r376346075/fulltext.pdf [retrieved on Nov. 16, 2010] Section 3; p. 1039.

* cited by examiner

MACHINE-LEARNING-BASED ADDITIVE MANUFACTURING USING MANUFACTURING DATA

TECHNICAL FIELD

The present invention relates generally to the field of software tools for additive manufacturing, and specifically to methods and systems for machine-learning-based additive manufacturing using manufacturing data.

BACKGROUND

Additive manufacturing is computer-controlled process of joining raw materials using a printer or other fabrication machine to fabricate physical objects from three-dimensional (3D) model data, layer upon layer. Additive manufacturing can thus be contrasted with subtractive manufacturing methodologies, which fabricate physical objects by cutting away, burning away, or otherwise excising or removing material from a raw workpiece. For the purposes of this application, a raw material is a substantially homogenous material that has not already been formed into a useful shape. Additive manufacturing technologies include 3D printing, binder jetting, direct energy deposition, material extrusion from a heated nozzle mounted on a movable arm, powder bed fusion (including direct metal laser melting (DMLM), direct metal laser sintering (DMLS), electron beam melting (EBM), selective laser sintering (SLS), and selective heat sintering (SHS)), sheet lamination (including laminated object manufacturing (LOM) and ultrasonic additive manufacturing (UAM)), vat polymerization, and wire arc additive manufacturing. For the purposes of this application, additive manufacturing does not mean merely the assembly together of different prefabricated components that are not raw materials. An overall process still referred to as "additive manufacturing" can begin with additive manufacturing of a component but further include subtractive manufacturing steps. As an example, additive manufacturing can require the fabrication of support structures to support the deposition of overhang structures, which support structures are not intended to form part of the finished fabricated object and therefore must be removed, e.g., by manually cutting them away or using ultrasonic energy to dissolve them. A process can still be referred to as additive manufacturing even though it may include such a subtractive postprocessing step.

Machine learning (ML) is a subset of artificial intelligence (AI) in which a computer uses algorithms and statistical models to accurately perform tasks without using explicitly coded instructions after having after having analyzed a learning or training data set, in effect relying on patterns and inferences to generalize from past experience. Accordingly, ML-based systems can be capable of solving problems not previously seen or considered and for which it would not be possible to code for every individual case. Types of ML algorithms include, among others, unsupervised learning and feature learning. Types of ML models that can be trained on the training data include artificial neural networks, decision trees, support vector machines, regression analysis models, Bayesian networks, genetic algorithms, principal components analysis, and cluster analysis.

A distributed ledger is a consensus of replicated, shared, and synchronized digital data spread across multiple networked computer systems, having no central administrator or centralized data storage. A blockchain is a distributed ledger comprising a growing list of records, called blocks, that are linked using cryptography, each block containing a cryptographic hash of a previous block, a timestamp, and transaction data (represented, e.g., as a Merkle tree). Once recorded, data in any given block cannot be altered retroactively without alteration of all subsequent blocks, which requires consensus of the networked computer systems on which the ledger is decentralizedly stored. A private blockchain is one that is permissioned, restricting participant and validator access to those invited by a network administrator.

SUMMARY

One example includes a machine-learning-based additive manufacturing method. The method can include processing, with a machine-learning model, an input vector describing a new part transaction to provide at least one part optimization output and at least one command initiation output to configure additive manufacturing of a new part. The machine-learning model is trained based on entries in a user experience database, entries in the user experience database each including at least data defining requirements for an additively manufactured part previously fabricated or attempted to be fabricated, specifications describing an additive manufacturing fabrication device, a selection of a raw material type fed to the fabrication device for fabrication of the additively manufactured part previously fabricated or attempted to be fabricated, a fabrication spatial orientation of the additively manufactured part within the fabrication device, a fabrication slicing resolution of the additively manufactured part, and a toolpath taken by the fabrication device in fabricating the part. The method further includes fabricating the new part using additive manufacturing based on the at least one part optimization output and the at least one command initiation output.

Another example includes a system for machine-learning-based additive manufacturing. The system can include a user experience database stored on or distributed across one or more non-transitory computer-readable memories. Entries in the user experience database each include at least data defining requirements for an additively manufactured part previously fabricated or attempted to be fabricated, specifications describing an additive manufacturing fabrication device, a selection of a raw material type fed to the fabrication device for fabrication of the additively manufactured part, a fabrication spatial orientation of the additively manufactured part within the fabrication device, a fabrication slicing resolution of the additively manufactured part, and a toolpath taken by the fabrication device in fabricating the part. The system further includes a processor configured to execute instructions implementing a machine-learning model trained based on the entries in the user experience database. The machine-learning model is configured to process an input vector describing a new part transaction to provide at least one part optimization output and at least one command initiation output to configure additive manufacturing of a new part.

Yet another example includes one or more computer-readable media configured to provide a computer as the system set forth above, or to execute in conjunction with a computer the method set forth above. Such an example can include one or more non-transitory computer-readable media storing instructions that when executed by a computer processor, cause the processor to process, with a machine-learning model trained on a user experience database comprising a plurality of entries, an input vector describing a new part transaction to provide at least one part optimization output and at least one command initiation output to configure additive manufacturing of a new part. Entries in the user experience database each include at least data defining requirements for an additively manufactured part previously fabricated or attempted to be fabricated, specifications describing an additive manufacturing fabrication device, a selection of a raw material type fed to the fabrication device for fabrication of the additively manufactured part, a fabrication spatial orientation of the additively manufactured part within the fabrication device, a fabrication slicing resolution of the additively manufactured part, and a toolpath taken by the fabrication device in fabricating the additively manufactured part.

DETAILED DESCRIPTION

Figure 1:
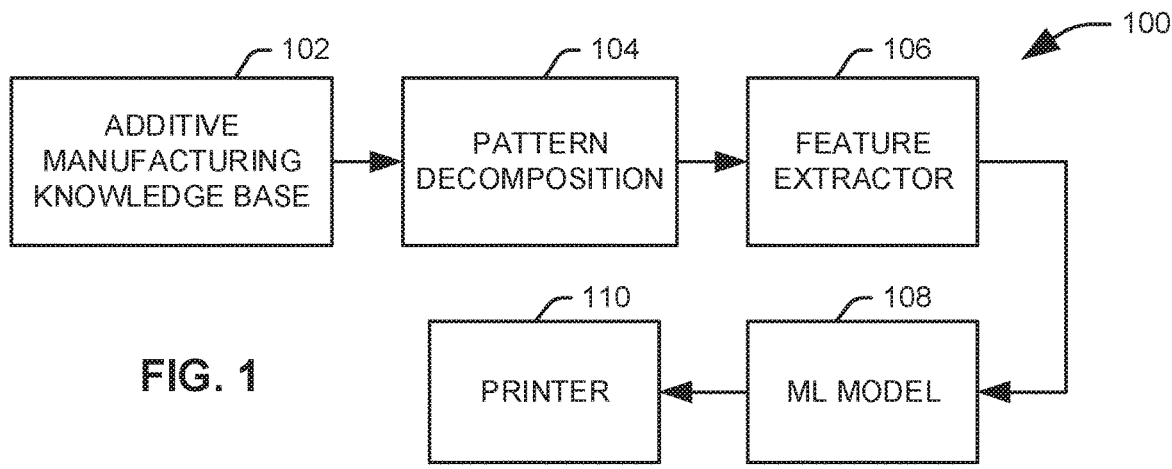
FIG. 1 is a functional block diagram of an example system for machine-learning-based additive manufacturing using manufacturing data.

Enterprises may produce additively manufactured parts or assemblies either as products themselves for sale to customers, or as in-house prototypes as a part of a new-product development cycle. However, additive manufacturing can be a highly heuristic and iterative process in that, for any given part or assembly, many additive manufacturing failures may occur before a success is achieved. A failure results when, after partial or complete additive manufacturing, an output part or assembly is not produced as expected or desired or does not meet required specifications or tolerances. Even when a part or assembly is successfully produced by additive manufacturing, the production may have been wasteful in the sense that more than a necessary amount of resources, including printer time, post-processing time, or raw materials, are consumed in the production than if the part had been produced in a more optimal fashion, that is to say, with better choices regarding part orientation, print resolution, and material type selection, among other preproduction processing and print settings. Typical causes of additive manufacturing failures or suboptimalities are too numerous to list exhaustively, but can include faulty or suboptimal part printing orientation or faulty or suboptimal support structure placement or design. On the other hand, care in extracting customer requirements, understanding printer specifications and settings, selecting the proper material, and properly converting a model file to a stereolithography file format can ensure successful part fabrication.

Each failure or suboptimal success equates to wasted personnel and printer time and/or raw material, but may also add to the "lessons learned" and "tribal knowledge" accumulated in the course of the trial and error of the additive manufacturing process. This accumulated knowledge may be useful for informing the additive manufacturing of future iterations of the same part or assembly, or wholly new parts or assemblies, but if not documented and disseminated in a systematic way, may remain only as private know-how within the personal experience of one or a few individual additive manufacturing personnel members ("users"), making it less useful to the larger enterprise that may have need to additively manufacture many more parts or assemblies than any single individual, or several or all the knowledgeable users within the enterprise's personnel, can be consulted on. Even if well-documented and disseminated using conventional means such as written reports published internally or stored on a fileserver in a computer network, such accumulated knowledge may remain inaccessible in practical terms for use in improving future iterations or new parts or assemblies given the impracticality of any one personnel member, confronted with a large electronic directory or database of documentation containing perhaps thousands or millions of reports, knowing where to find desired knowledge or even knowing that such knowledge may exist in the directory or database. Furthermore, conventional knowledge storage means do not provide a ready way for the knowledge stored therein to become iteratively stronger for any given part or assembly with each additive manufacturing production job, in a way that can be usefully implemented to improve future production job outcomes.

The systems and methods depicted in the appended drawings and described herein enable automated re-use of accumulated additive manufacturing knowledge within an enterprise or organization by storing the knowledge in a database, for example, as a blockchain, training machine learning model on the accumulated knowledge, and applying the trained machine learning model to new additive manufacturing projects and tasks to provide improved additive manufacturing outcomes, thereby reducing failures and the wastefulness associated with suboptimal additive manufacturing production. A private ledger can function as an open-source, blockchain-based distributed platform containing lessons learned and tribal knowledge on each additively manufactured part or assembly ever produced within the enterprise or organization. Each ledger block can include various manufacturing knowledge, including information such as part geometry, build parameters and orientation, failure analysis modeling, lessons learned, tribal knowledge, processing software, machinery used, finite element method (FEM)/finite element analysis (FEA) models, defects, flaws, and images. The ledger can become iteratively stronger with each participant input. The records in the ledger can be linked and secured via cryptography, that is, the ledger can be a blockchain.

The numerous lessons learned and technical tricks that can be applied to an additive manufacturing process that would make the next experience more productive and/or less wasteful can be collected in a historical record shared by a plurality of users, e.g., within an enterprise or organization. As the historical record becomes richer and more expansive with learning experiences being added to it, a system including a machine-learning model trained on the historical record can either automatically apply a learned real-time corrective action or or can recommend a modification to a user before a manufacturing command is initiated, e.g., to start a 3D printer. The systems and methods described herein can thereby increase the probability of a successful additive manufacturing experience and/or improve the quality of an object or assembly additively manufactured thereby. The described systems and methods can reduce the number of print production jobs or runs of print production jobs needed to achieve an acceptable output, thus lowering cost of fabrication.

The described systems and methods are capable of drawing upon the resource of a large, potentially worldwide historical population base. The machine learning model can be trained on the parameters described along with a defined set of completed part transactions, facilitating its ability to reach an accurate conclusion when presented with a new part build challenge.

FIG. 1 illustrates a functional block diagram of an example system 100 for machine-learning-based additive manufacturing using manufacturing data. The system 100 can be implemented on one or more physical devices (e.g., servers) that may reside in a cloud computing environment or on a computer, such as a laptop computer, a desktop computer, a tablet computer, a workstation, or the like. In the present example, although the components 102, 104, 106, 108, and 110 of the system 100 are illustrated as being implemented on a same system, in other examples, the different components could be distributed across different systems and communicate, for example, over a network, including a wireless network, a wired network, or a combination thereof. The system 100 includes, as a data source, an additive manufacturing knowledge base 102 that can be accessed to provide additive manufacturing fabrication parameters and measured or recorded additive manufacturing production outcome data to a pattern decomposition component 104. The additive manufacturing knowledge base 102 can include, for example, any of a storage medium accessible by a local bus or a network connection, or a user interface at which a user can enter information from one or more previous additive manufacturing production jobs. In some examples, knowledge base 102 is a relational database stored on a single central system or distributed over several systems. In some examples, knowledge base 102 is a distributed ledger. In some examples, knowledge base 102 is a blockchain, that is, knowledge base 102 can be a database stored in blockchain format, having each entry in the database stored as a timestamped block of a distributed ledger. In some examples, knowledge base 102 is a private blockchain, configured such that only authorized users within the enterprise or organization can write to and/or read from it.

Figure 4:
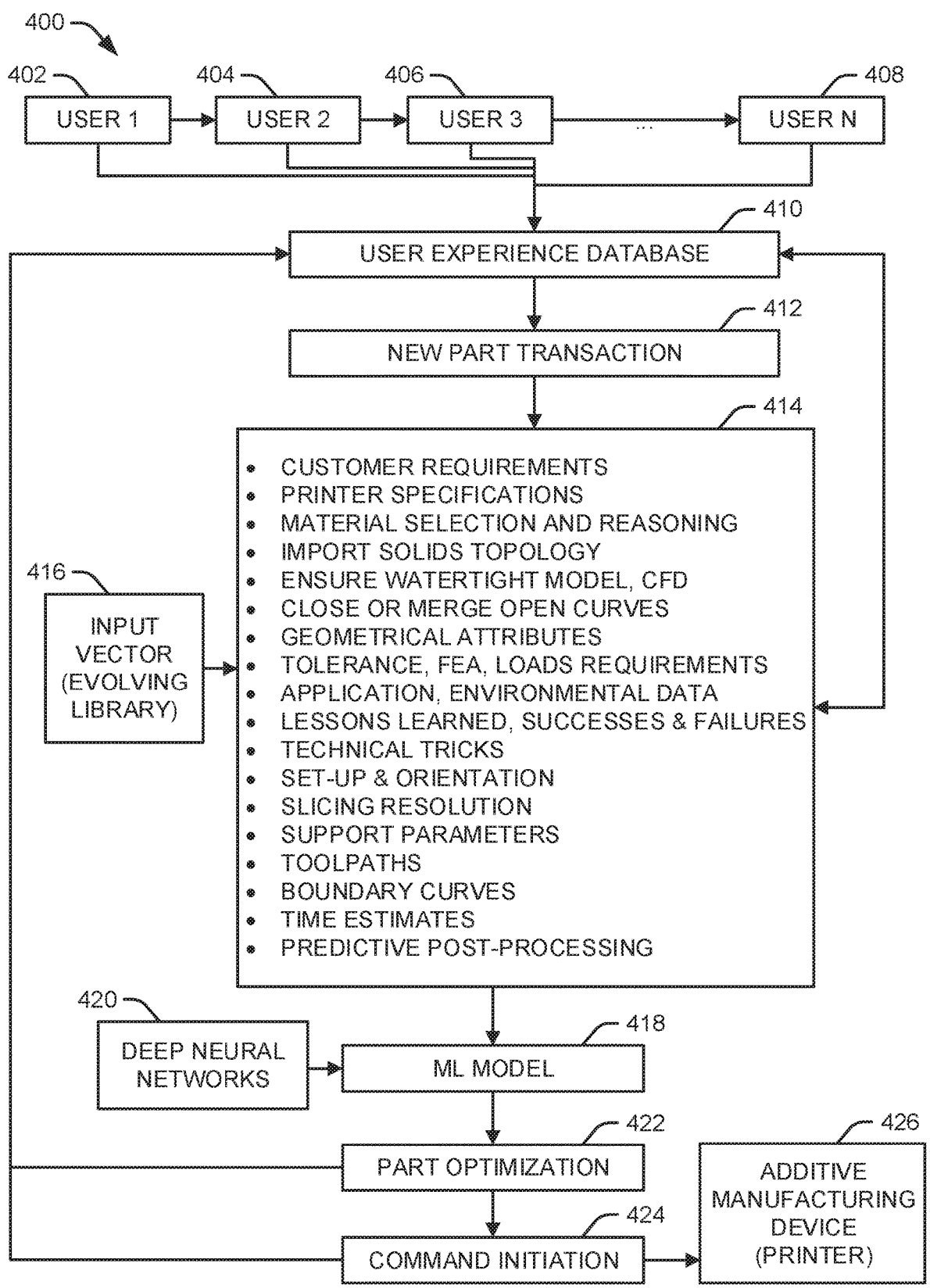
FIG. 4 is a flow diagram illustrating an example of machine-learning-based additive manufacturing.
Figure 5A:
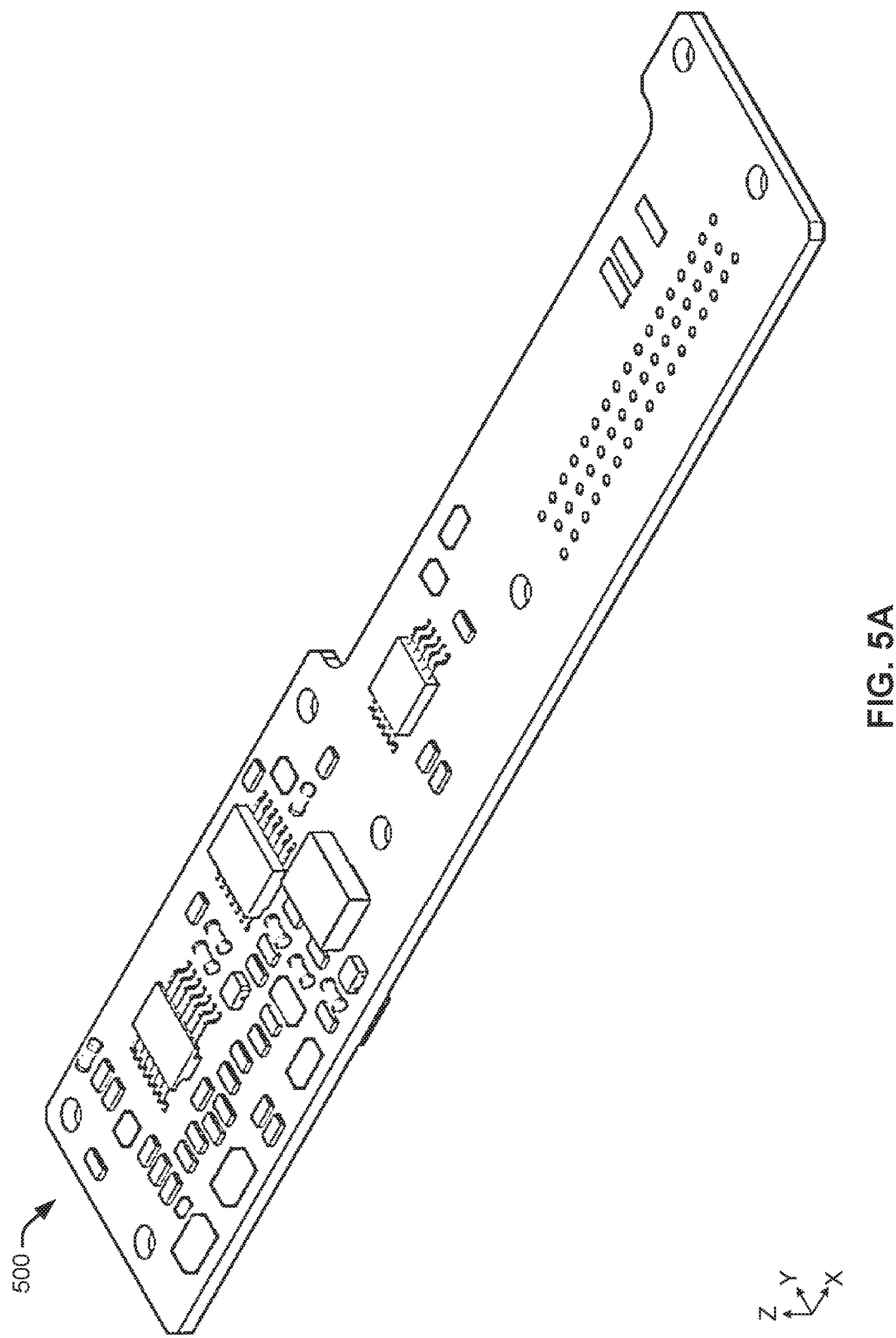
FIGS. 5A-5D respectively show perspective and various plan views of a 3D model of an example circuit board mockup for additive manufacturing fabrication.
Figure 5B:
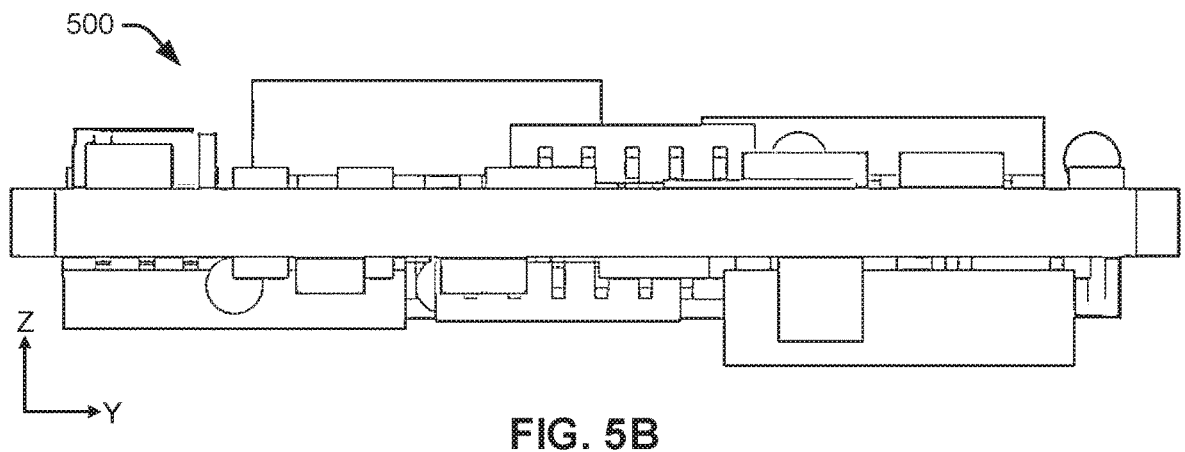
Figure 5C:
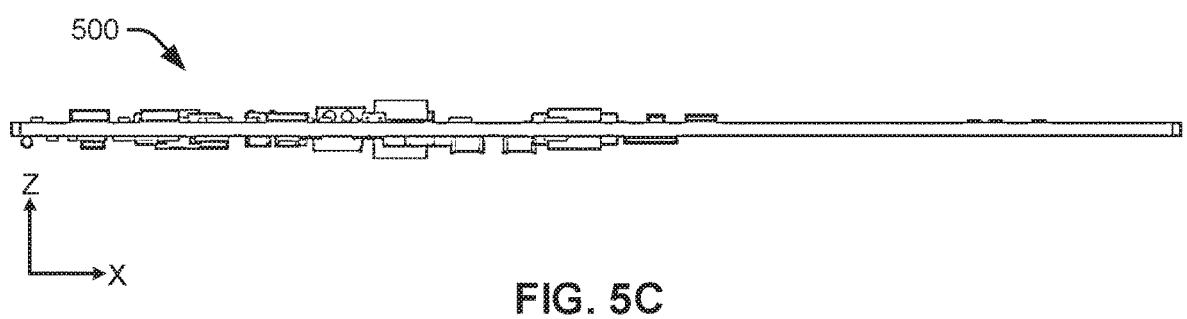
Figure 5D:
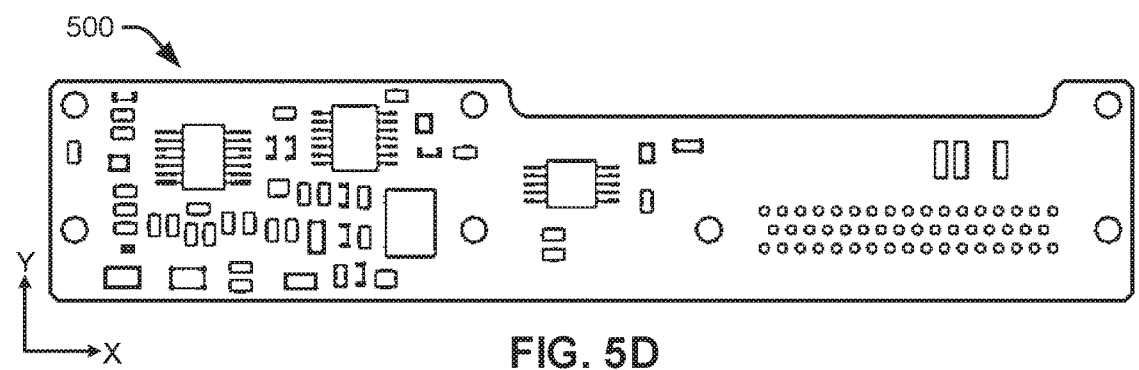

A pattern decomposition component 104 is programmed to decompose a set of additive manufacturing data representing a past additive manufacturing experiences, including information representative of objects or assemblies being printed, information representative of printer settings, and information representative of print outcomes. The word "print" is used inclusively here to refer to any type of additive manufacturing modality and not just 3D printing. A new vector of additive manufacturing data can, for example, be decomposed into a linear combination of basis vectors to provide a set of coefficients representing the additive manufacturing data. An example listing of types of additive manufacturing data fields 414 is illustrated in FIG. 4.

A feature extractor 106 generates a feature vector that includes at least one of the set of coefficients generated at the pattern decomposition component 104. A machine learning model 108 determines at least one prefabrication model adjustment parameter and/or print setting parameter for a new print job and/or at least one print job outcome estimate from the metric. As examples, not meant to be an exhaustive list, the prefabrication model adjustment parameter can represent a print orientation of a component or assembly to be printed in a print job, a number of layers to be used or a layer thickness or thicknesses, a geometry parameter descriptive of how a three-dimensional model is divided for printing during a prefabrication model processing phase, or information controlling the placement or geometry of support structures added to the model during a prefabrication model processing phase. As examples, not meant to be an exhaustive list, the print setting parameter can represent a material to be used for the job, a particular printer or model of printer to be used, a nozzle aperture thickness or temperature, or any of a number of other parameters that may be accessible for modification on a 3D printer or other additive manufacturing fabrication device. As examples, not meant to be an exhaustive list, the outcome estimate can be an estimate of print time for the job, an estimate of raw material usage for the print job, or an estimate of the likelihood of success of a print job. The prefabrication model adjustment parameter or print setting parameter provide or contribute to part optimization or command initiation, respectively. The prefabrication model adjustment parameter, print setting parameter, and/or outcome estimate provided by the machine learning model 108 can be stored on a non-transitory computer-readable medium associated with the system 100 and/or provided to a user at a display via a user interface (not shown in FIG. 1, but see FIG. 2).

Figure 2:
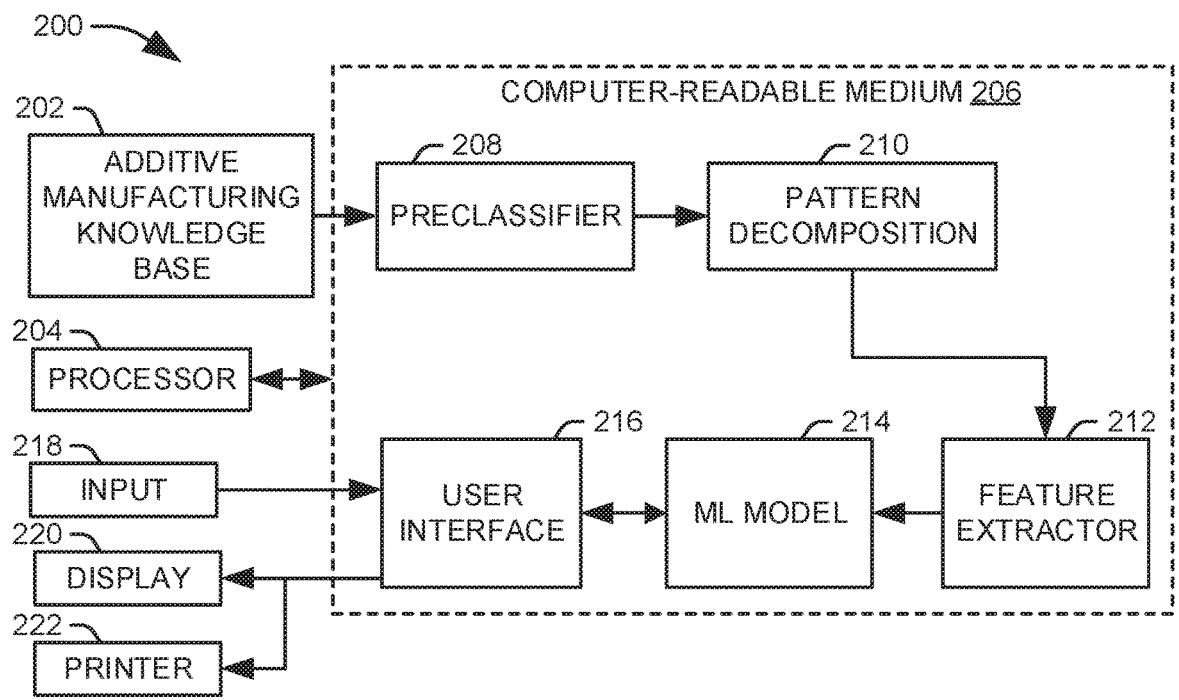
FIG. 2 is a functional block diagram of an example system for machine-learning-based additive manufacturing using manufacturing data.

FIG. 2 illustrates a functional block diagram of an example system 200 for machine-learning-based additive manufacturing using manufacturing data. To this end, the system 200 incorporates a machine learning model 214 that utilizes features generated from a decomposition of additive manufacturing data into archetypal parameters to generate a categorical or continuous additive manufacturing parameter representing a change to a prefabrication model processing adjustment or a setting for a 3D printer or other additive manufacturing fabrication device. In the illustrated implementation, an additive manufacturing knowledge base 202 provides additive manufacturing data regarding one or more past print jobs or print runs to a data analysis component implemented as a general-purpose processor 204 operatively connected to a non-transitory computer-readable medium 206 storing machine-executable instructions. In the illustrated system 200, the additive manufacturing data can include not only part programming information but also specific machine or software variables. An input device 218, such as a mouse or a keyboard, can be provided to allow a user to interact with the system 200, including to input or modify additive manufacturing data, and a display 220 can be provided to display additive manufacturing data and calculated parameters to the user.

In the illustrated example 200, the machine-executable instructions include a preclassifier 208 that classifies a print job into one of a plurality of categories representing different levels of complexity or types of object to be 3D-printed or otherwise additively manufactured. The preclassifier 208 can utilize any appropriate classification model for this determination, for example, creating a probability distribution to classify parts based on part geometry, or in a simple example, the preclassifier can base the preclassification on one or more user-generated variables stored in the additive manufacturing data in the knowledge base 202 explicitly specifying a complexity and/or type category.

A pattern decomposition component 210 can be programmed to decompose the additive manufacturing data into a linear combination of a defined basis set of additive manufacturing data patterns to generate a set of coefficients characterizing the additive manufacturing data, as in the system 100 of FIG. 1. The defined basis set can, for example, be defined via archetypal analysis over a corpus of additive manufacturing data. In the illustrated example, however, multiple basis sets can be generated, each representing one of the plurality of categories associated with the preclassifier 208. The basis set used at the pattern decomposition component 210 for each print job can therefore be assigned according to the category assigned to that print job at the preclassifier 208. FIGS. 5-11, discussed below, illustrate prefabrication model processing of an example print job.

The set of coefficients from the pattern decomposition component 210 can be provided to a feature extractor 212 to generate a feature vector representing a given past print job. Where multiple sets of additive manufacturing data are acquired for successive iterations of a print job over time, a change, measure of central tendency, or measure of deviation for any of the values in the additive manufacturing data can also be used in the feature vector.

The machine learning model 214 can utilize one or more pattern recognition algorithms, implemented, for example, as classification and regression models, each of which analyze the extracted feature vector to assign one or more prefabrication or fabrication parameters or outcome estimates to a job. Once trained, and fed information regarding a new part to be fabricated, the machine learning model can, in effect, automatically make suggestions or decisions on a probable optimal part print orientation (dictating how the new part should be oriented in three-dimensional space for fabrication); on the type, placement, and characteristics of support structures needed to be added to a model prior to its printing; on slicing mechanisms; on deposition layers; on one or more toolpaths; and/or on one or more boundary curves (as examples of suggestions or decisions). The prefabrication or fabrication parameters or outcome estimates can be categorical or continuous. For example, a categorical parameter can represent a selected material type or a model of printer to be used for a print job. A continuous parameter can represent, for example, a model orientation, a number of layers to be used for a job, a layer thickness, various geometry parameters used in prefabrication model processing, an estimate of print time, or an estimate of a likelihood of success for a print job.

Where multiple classification and regression models are used, the machine learning model 214 can include an arbitration element that can be utilized to provide a coherent result from the various algorithms. Depending on the outputs of the various models, the arbitration element can simply select a class from a model having a highest confidence, select a plurality of classes from all models meeting a threshold confidence, select a class via a voting process among the models, or assign a numerical parameter based on the outputs of the multiple models. Alternatively, the arbitration element can itself be implemented as a classification model that receives the outputs of the other models as features and generates one or more output classes for the print job.

The machine learning model 214, as well as any constituent models, can be trained on training data representing the various classes of interest. The training process of the machine learning model 214 will vary with its implementation, but training generally involves a statistical aggregation of training data into one or more parameters associated with the output classes. Any of a variety of techniques can be utilized for the models, including support vector machines (SVN), regression models, self-organized maps, fuzzy logic systems, data fusion processes, boosting and bagging methods, rule-based systems, or artificial neural networks (ANN).

For example, an SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. An SVM classifier utilizes a user-specified kernel function to organize training data within a defined feature space. In the most basic implementation, the kernel function can be a radial basis function, although the systems and methods described herein can utilize any of a number of linear or non-linear kernel functions.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

A regression model applies a set of weights to various functions of the extracted features, most commonly linear functions, to provide a continuous result. In general, regression features can be categorical, represented, for example, as zero or one, or continuous. In a logistic regression, the output of the model represents the log odds that the source of the extracted features is a member of a given class. In a binary classification task, these log odds can be used directly as a confidence value for class membership or converted via the logistic function to a probability of class membership given the extracted features.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used, but a continuous parameter can be computed according to a number of decision trees that select a given task.

Regardless of the specific model employed, the prefabrication model adjustment parameter, print setting parameter, and/or outcome estimate generated at the machine learning model 214 can be provided to a user at the display 220 via a user interface 216, stored on the non-transitory computer readable medium 206, for example, in a file or database or database entry associated with the print job, or output to a printer 222 to configure, schedule, or execute a print job or run of multiple print jobs.

Figure 3:
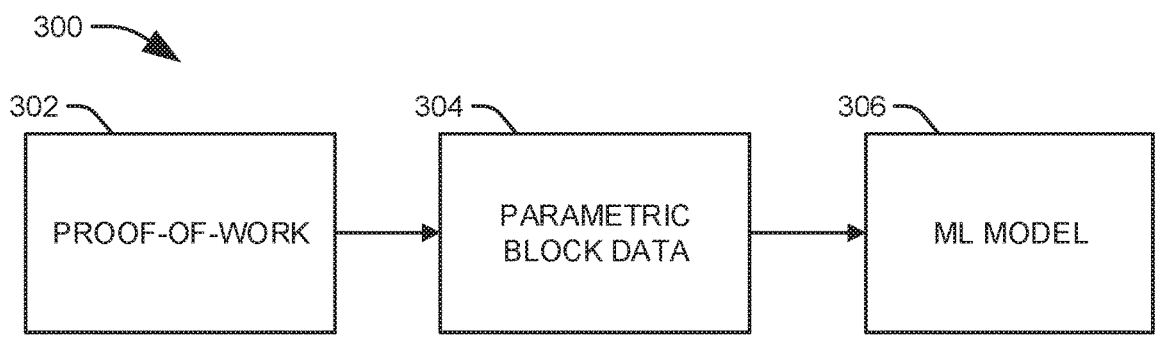
FIG. 3 is flow diagram illustrating an example training of an additive manufacturing machine learning model.

FIG. 3 illustrates a basic flow diagram of an example training of a machine-learning model for additive manufacturing. For each proof-of-work 302, information is populated in an additive manufacturing knowledge base, e.g. a distributed ledger, as parametric block data 304. A proof-of-work is an additively manufactured part that has been processed, completed, and successfully used or delivered to a customer. Any given completion constitutes a part transaction, which can be recorded in the knowledge base. A proof-of-work chain is a blockchain ledger comprising a plurality of part transactions for parts produced by an enterprise or organization, each part transaction being a timestamped block in the chain. The proof-of-work chain thereby collects information on how a part was "transacted"—how it was created, how it was built, what was the resource burden/expense involved in making the part, and what type of difficulties were encountered in successfully making the part. In practice, the proof-of-work chain can constantly collect part transaction information, just as a blockchain used in a cryptocurrency constantly collects currency ownership transfer transactions. The more user data accumulated in the knowledge base, the longer the proof-of-work chain, and the stronger the knowledge base and its parametric block data 304 become as a mechanism for training the machine-learning model 306.

Implementing the knowledge base as a distributed-ledger proof-of-work chain can provide benefits of decentralization, encryption, and security over what may be provided with a centralized data repository. However, even if implemented in the form of a blockchain, the proof-of-work chain need not necessarily be stored in a decentralized manner, distributed among a number of different computer systems; the proof-of-work chain can in some examples be stored on a single central data server. Even in such case, the proof-of-work chain can pull additive manufacturing data from a plurality of geographically different additive manufacturing sites. In this manner, the blockchain form of the proof-of-work chain can provide benefits to the geographically distributed enterprise or organization even in the case that the proof-of-work chain is ultimately stored centrally.

FIG. 4 illustrates an example of a machine-learning-based additive manufacturing process 400. Over the course of a plurality of additive manufacturing jobs, a number of users 402, 404, 406, . . . 408 contribute to a user experience database 410 by inputting fabrication parameters and outcome information. User experience database 410 can correspond, for example, to knowledge base 102 of FIG. 1 or knowledge base 202 of FIG. 2. An example listing of the types of information that can be parametrized and stored in the database 410 is provided in box 414. The user experience database 410 can also be updated in an automated fashion from part optimization information 422 or command initiation information 424 provided by the machine-learning-based additive manufacturing process 400, e.g., by instructions used to preprocess a three-dimensional model to prepare it for 3D printing, or commands to be issued to a printer or print controller as part of a machine-learning-based additive manufacturing system.

Having access to the user experience database 410, a user or operator can initiate a new part transaction 412 based on a customer order or in-house request. A variety of information may be associated with the new part transaction 412, examples of which information are non-exhaustively listed in box 414.

"Customer requirements" can include information about the manner in which an ordered part may be used, the required dimensions, geometry, and curvature of the part (which may be specified by a model file), and why the customer has ordered the part to be additively manufactured as opposed to manufactured using more conventional fabrication techniques (e.g., machining out of a block of metal). Such data can include structed data pertaining to demonstrations, functional prototypes, conceptual models, simulation, testing, design improvements, proposals, mock-ups, tooling, and assembly planning. Also within this category can be information about loads or clamping pressures expected to be applied to the finished part, whether the part will be used for tooling, whether the part will be used as a prototype or demonstration part or, conversely, whether the part will be expected to function in a production or mission environment. The model file may be, for example, a computer-aided design and computer-aided manufacturing (CAD/CAM) file, a CATIA file, a Creo Elements (formerly Pro/ENGINEER) file, or an NX file.

"Printer specifications" can include the printer manufacturer; the chamber volume of a printer (also known as the build envelope), which dictates the maximum fabrication dimensions of a part; maximum printer layer resolution capabilities; printer accuracy and tolerances; types of material accepted (that a printer is capable of printing in); software platforms supported by the printer; and printer calibration information.

"Material selection and reasoning" includes information designating or characterizing the raw material selected to be supplied to the 3D printer or other additive manufacturing device. As examples, types of materials can include ABS, ASA, ESD-7, Ultem 1010 resin, Ultem 9085 resin, Ultem 2300, Ultem PEI, Antero, polycarbonate, Nylon-12, carbon fiber, titanium alloy, PEKK, PPSU, PEEK, aluminum, and Inconel. The associated "reasoning" can beneficially help inform why the one material has been chosen over another. For example, if the fabricated part is to be used purely for show (e.g., as a demonstration component), then a less durable and consequently less expensive or easier to print raw material may be used. By contrast, if the fabricated part is to be used under production or mission conditions and is required to meet certain more stringent specifications for tensile strength, ruggedness, rigidity, flexibility, heat-resistance, scratch-resistance, or other use properties, then some different print raw material may be suggested.

A provided CAD file for a part may be in a Standard for the Exchange of Product model data (STEP) file format, commonly used for 3D models, that will require conversion to a stereolithography (STL) file format as part of a prefabrication process. An operator will have to ensure that all of the solids topology is correctly imported from the STEP file to the STL file format. An inaccurate conversion will result in a failed print. "Import solids topology" describes the import procedure (import steps and/or import settings) found or suggested to ensure that the model is imported in its correct form, with all the curves and solid features of the model accurately represented.

Fluid dynamics simulations can simulate the effects of a liquid environment over a model to be fabricated to ensure that all pieces of a part, including smaller components of the part expected to be solidly attached to a main structure of the part, will, in fact, be solidly attached when the part is done printing. Information regarding these simulations is encapsulated in the "ensure watertight model, computation of fluid dynamics (CFD)" category of data associated with a job. As an example, if a part to be fabricated is a mockup of a printed circuit board, as in the example illustrated in FIGS. 5-11, it may be the case that the circuit board mockup may include capacitors and other small components printed along with the circuit board which, after printing, may not be firmly attached as desired, such that the small components may be loose or fall off of the printed mockup. CFD simulations help to catch such model glitches so that the model can be corrected prior to printing, for example, by adjusting the model to add additional material between model subcomponents to ensure their solid connection with each other after printing.

Open curves are faults in the geometry of models designed with wireframes or solids; a part designer may design a part that has open curves in its CAD model, which CAD model may be passed on to an additive manufacturing operator for printing However, 3D printing software and printers do not recognize and cannot print open curves in a model. Open curves can be closed manually or with special software routines. The "close or merge open curves" category in the knowledge base can store information about such faults in a model and the corrective actions taken to repair them as part of the preproduction phase.

"Geometrical attributes" include the X-Y-Z dimensions of a part, the curvatures, contours, and/or splines of the part, part thicknesses, determinations that a part or portions of the part that may be too thin to be printed, depending on print resolution, and the like. Information related to dimensional tolerances for a part or portion thereof, and stresses and strains expected to be supplied to a part, can fall under the "tolerance, finite element analysis (FEA), loads requirements" category and likewise can be stored in the knowledge base, and can include information pertaining to specific machine accuracies, thermal nature of FDM process, post-machining, hard mounting points, press-fit bushings and pins, abrasion, threaded inserts. This information can play a role in the material type selection and the density of the material.

Under the category of "application, environmental data" is such information as whether the part will be intended to be used for tooling, ground support, or outside (and thus exposed to elements such as sunshine, wind, rain, snow, freezing/thawing), inside, a clean room environment, a laboratory environment, under water, under pressure, under heat, under saline or acid conditions, etc. Such information includes information pertaining to design evolution, tooling, demonstrations, testing, fit-checks, infrastructure, UV effects, weight and durability considerations, tool assembly, part bonding, integrating inserts and bushings, working environment, tolerances, hard-mounting points, datums, static and dynamic loading, handling, in-service temperatures, chemical compatibility, material creep behavior, interactions, aesthetics, and surface roughness (Ra). This information can likewise play a role in the material type selection and the density of the material.

Information stored under the categories of "lessons learned, successes & failures" are mistakes made by operators in past production runs which led to print failures or, conversely, felicitous choices that resulted in an exceptional job completion (an "epic"). Such information can include, for example, file conversion steps or settings that resulted in inaccurate file conversion, printer settings that resulted in a print failure including inadequate or overkill choice of resolution, incorrect orientation(s), inadequate support structure design(s), poor choice of material(s), etc. Other "lessons learned" can include an orientation found to be best, a Z height with respect to base area, contour, loft, curvature, material behavior information, post-processing steps, and ultrasonic tank effects. "Technical tricks" include tribal knowledge and personal secrets regarding special setups that experienced operators use to produce parts that are difficult to produce, which information is never or rarely passed down from the experienced operator to a new user. Information under these categories can be encoded in a parametrized form by a user or can be stored in a natural language narrative form that can be automatedly analyzed and digested to numerical form using natural language processing to further the training of the machine-learning model 418 or the model's processing of a new part transaction 412.

In general, a part printed tall will require more support structure material and/or will have a greater risk of print failure than a part printed flat. Information under the category of "set-up & orientation" includes information regarding a three-dimensional orientation of a part chosen to maximize ease of printing, e.g., with the least amount of support structure material required, and/or with the least chance of part printing failure. Such information can be expressed, for example, as a set of angles and/or offsets given with respect to origin axes in a model file. Under this category is information pertaining to build orientation to maximize material in X-Y direction, slice parameters, part interior style, visible surface style, support styles and base, wall stabilization, anchor columns, self-supporting angles, toolpath setup, boundary curves, vertical versus horizontal holes, and resolution.

Additive manufacturing involves the laying down of material in layers called slices to build parts layer by layer (slice by slice). Many 3D printers offer the option of printing slices at resolutions of 5,000ths, 7,000ths, 10,000ths, and 13,000ths of an inch, with the tradeoff that finer resolution printing can take more printing time. Mockups, for example, can generally be printed at coarser resolution, whereas components expected to be used in a production or mission setting may need to be printed at a finer resolution. The "slicing resolution" category can store the selected print resolution parameter for a given job.

"Support parameters" carries information used in automatically generating support structures added to a model during a preproduction phase to ensure that overhanging components in the model are adequately printed. "Toolpaths" carries information regarding the raster pattern used to print each slice, that is, the path of movement taken by a print head in the course of printing. "Boundary curves" carries information about the periphery of the part (potentially including inner peripheries of holes in a part), expressed, for example, as a parametric equation. Based on many of the above factors, including resolution, model size and density, amount of support, material type, printing software can generate estimates of how long it will take to print a given part, which information can be stored in the knowledge based under the "time estimates" category. Some parts, for example, can take upwards of 200 hours of continuous printing to complete. The differences between estimated time and actual print time can also be stored under this category. Information stored in the "predictive post-processing" category can include information about how much support structure material will need to be removed from a printed part, how much time will be required to remove it, and by what methods it will need to be removed (e.g., manual cutting or ultrasonic dissolution), and/or what other assembly steps may be required after printing to provide a customer with a finished part as ordered. As examples, such post-processing information can include information pertaining to support removal through mechanical and ultrasonic tank means, plastic welding, threaded inserts, part bonding, bushings, and plating.

Thus, the user experience database 410 may store information in the above categories collected from a number of prior print production jobs. The machine-learning model 418 can be trained on this user experience database 410 using, for example, deep neural networks 420. An input vector 416 parametrizing any or all of the above information for a new part transaction 412 may be fed to a trained machine-learning model 418 for processing to determine part optimization outputs 422 and/or command initiation outputs 424, in either case modifying, updating, or filling the gaps in input vector 416. Commands generated thereby can be sent to an additive manufacturing device 426 such as a 3D printer to program the printer for a print job. In some cases, such outputs 422, 424 can be provided as suggestions to a human operator for confirmation prior to carrying out steps that would preprocess a model file or program a printer for a print job.

Machine-learning model 108, 214, 306, or 418 can thus record information generally relating to part programming, on the one hand, and specific machine variables and/or specific software variables on the other hand. In this context, part programming can consist of (1) configuring the 3D printer; (2) orienting the STL model (CAD converted to a stereolithography format); (3) "slicing" the STL model by intersecting the STL model with a series of horizontal planes to create slice curves; (4) creating support curves, defining where temporary supports will be built in the part, which supports will ultimately be disposed of; (5) creating toolpath fill for model and support curves; (6) saving a toolpath file; and (7) downloading the toolpath file to the printer for part building. Specific machine variables and/or specific software variables can consist of fabrication-machine-specific calibration values; head motor currents; head purge and control parameters; autoload parameters; stepper motor currents; XYZ axis speed parameters; purge and tip wipe locations; head temperature setback and no-ooze parameters; end of curve and purge following error monitoring; head and chamber temperatures used during model build; head velocities; distance between slices (in inches); minimum and maximum speeds to move the head (in inches per second); origin: X & Y coordinate location to start the model; clearance move: amount to raise the head during glueless moves (in inches); delay time and encoder tick rate (in milliseconds, flowrate); fluid relaxation time during acceleration/deceleration; desired flow accuracy during acceleration/deceleration. In turn, the machine-learning model 410 can produce the part optimization and command initiation outputs 422, 424 based on training from the above parameters as stored in the user experience database 410 (which can take the form of a blockchain) and the input vector 416. In other words, the machine-learning model can be capable of performing the part programming and the parameter setting in an automated way for a new part job based on the past part job data.

An example operation of a machine-learning-based additive manufacturing system according to the flow diagram of FIG. 4 is not described. New part transactions 412 are broadcast to the machine-learning model 418. The proof-of-work historical record of the user experience database 410 compiles new part transaction data into a block. The proof-of-work historical record becomes more resilient, richer with knowledge, and iteratively stronger with each block addition and feeds the machine-learning model 418, which is iteratively re-trained either with each block addition or periodically. The machine-learning model 418 provides real-time feedback on the next part transaction based on history. The machine-learning model 418 utilizes the notion of similarity and creates a mapping between, on the one hand, voxel data, orientation data, geometry data, technical language data, and fabrication device variables and parameters, and, on the other hand, the part to be 3D printed. These mappings can, for example, be represented within a structured probability distribution. The proof-of-work historical record 410, together with the machine-learning model 418, learns probable model orientation, support structure, toolpaths, and boundary curves based on input. The machine-learning model 418 utilizes neural networks and pattern recognition to make suggestions, predictions, and warnings. The machine-learning model 418 provides outputs 422, 424 that optimize user/object interaction.

FIGS. 5-11 illustrate an example process of a customer-requested 3D print of an integrated circuit board mockup for use in enclosure assembly planning. FIG. 5A is a three-quarters perspective view of a CAD model 500 of the circuit board. FIG. 5B is a right-side plan view of the CAD model 500 of the circuit board. FIG. 5C is a front plan view of the CAD model 500 of the circuit board. FIG. 5D is a top plan view of the CAD model 500 of the circuit board. In each of these drawings the illustrated indication of the axes should not be construed as indicating a model origin point that is consistent between the views. As can be seen, the model 500 includes a main subcomponent of a planar board and a variety of protruding subcomponents, such as integrated circuit (IC) packages ("chips") and capacitors. The CAD model 500 can be converted to an STL (stereolithography) format to be compatible with print processing software. The 3D printer will be configured by choosing the type of modeler, material, slice height, and extrusion tip.

Figure 6:
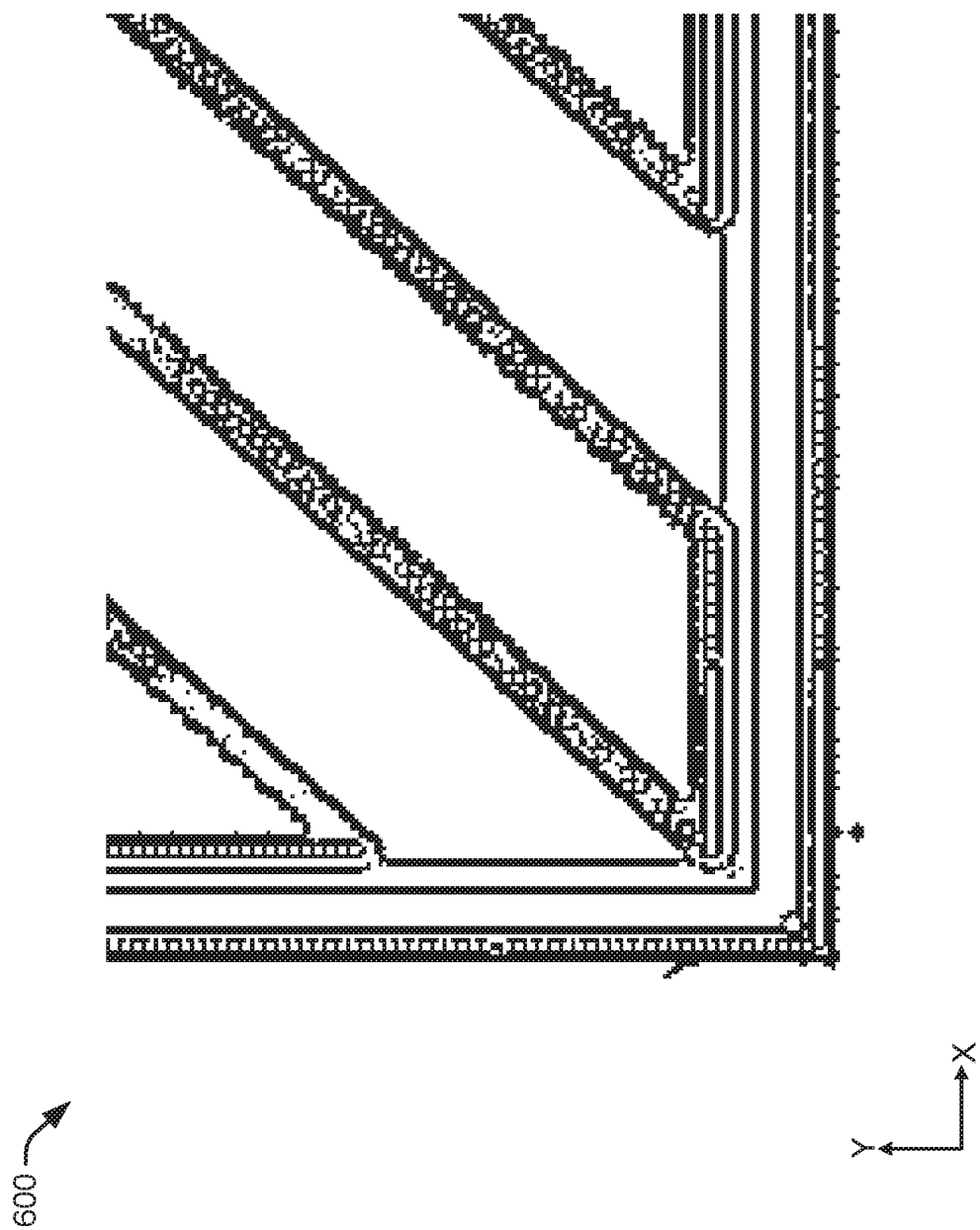
FIG. 6 shows a portion of a layer of the model of FIGS. 5A-5D after conversion to the stereolithography format using a sparse, low-density part build style.

The part build style can be configured as described. In the present example, a "Sparse, Low-Density" style can be chosen based on a review with the customer. This setting minimizes the amount of model material used by utilizing a uni-directional raster pattern with gaps between raster legs for interior regions. An example of the pattern is illustrated in FIG. 6, which shows a portion 600 of a layer of the model after conversion to the stereolithography format. Top and bottom exposed layers are built with the solid raster pattern. An extra contour is added to the part boundary and a separate contour encloses the uni-directional sparse rasters. For other print jobs, other build styles can be selected; "Solid" (fully dense raster toolpaths), "Sparse, High/Double-Dense" (crosshatch raster pattern), and "Hexagram" (tri-direction crosshatch raster pattern) options are also available. An "Enhanced" visible surface style can be selected, such that independent controls are provided for visible surface rasters and non-visible, internal rasters.

Figure 7:
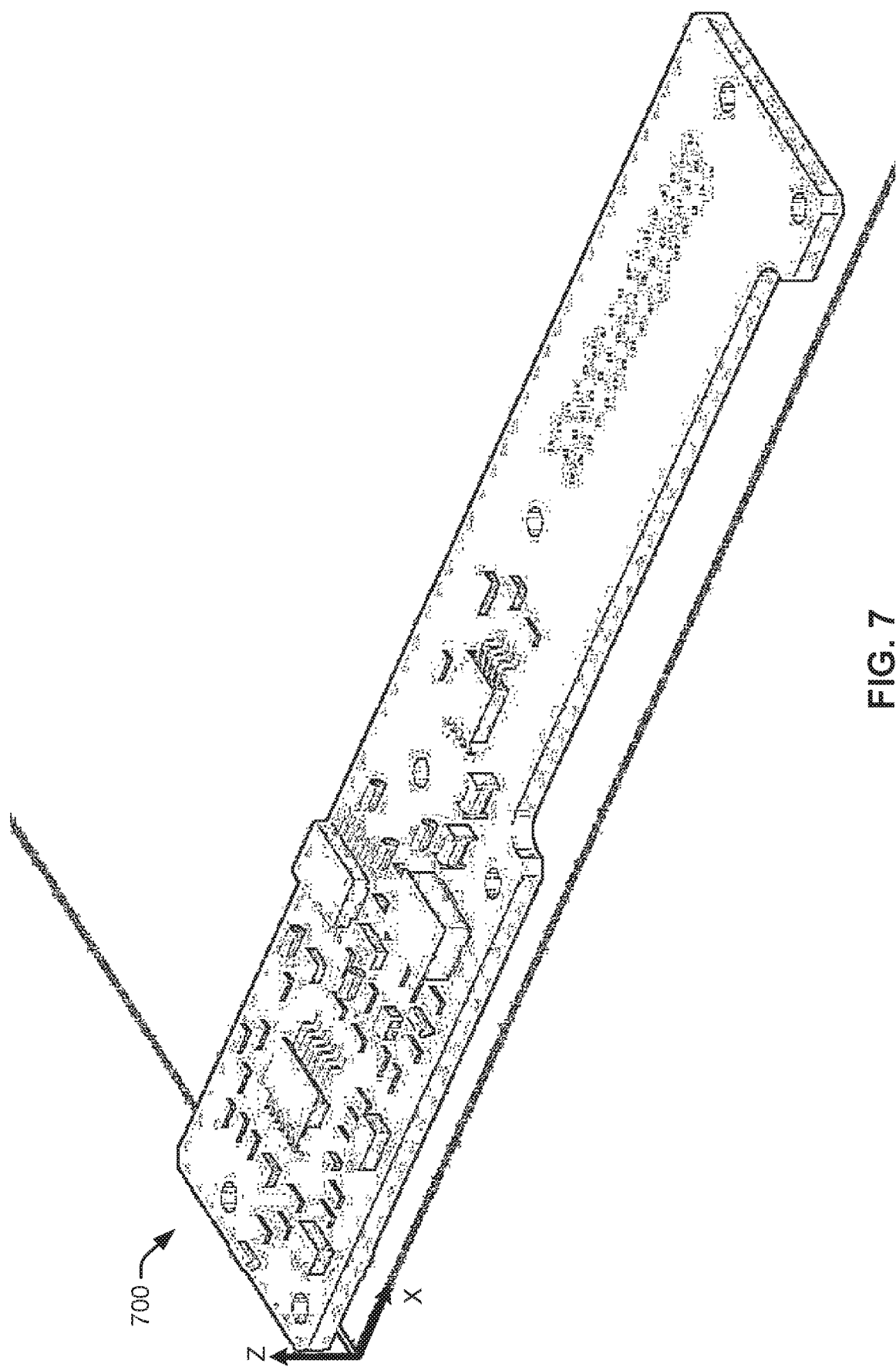
FIG. 7 is a perspective view of the model of FIGS. 5A-5D, re-oriented for fabrication.

Proper orientation affects both the build time and the appearance of the finished printed part. Depending on the shape of the part, it might also make the difference between whether or not the part fits inside the printer chamber envelope. To reduce build time, the part can be oriented such that minimal supports are needed. To give the best appearance for the part, the part can be oriented in a fashion where the slices are layered one on top of another along a vertical plane. In most cases, a part should be oriented to maximize area with respect to the XY-plane, as shown in FIG. 7. Note that the orientation of the part 700 in FIG. 7 is flipped over from the orientation shown in FIG. 5A. In the IC board orientation shown in FIG. 7, the XYZ origin coordinate at the upper left of the depiction represents the print head origin to start the model.

Figure 8:
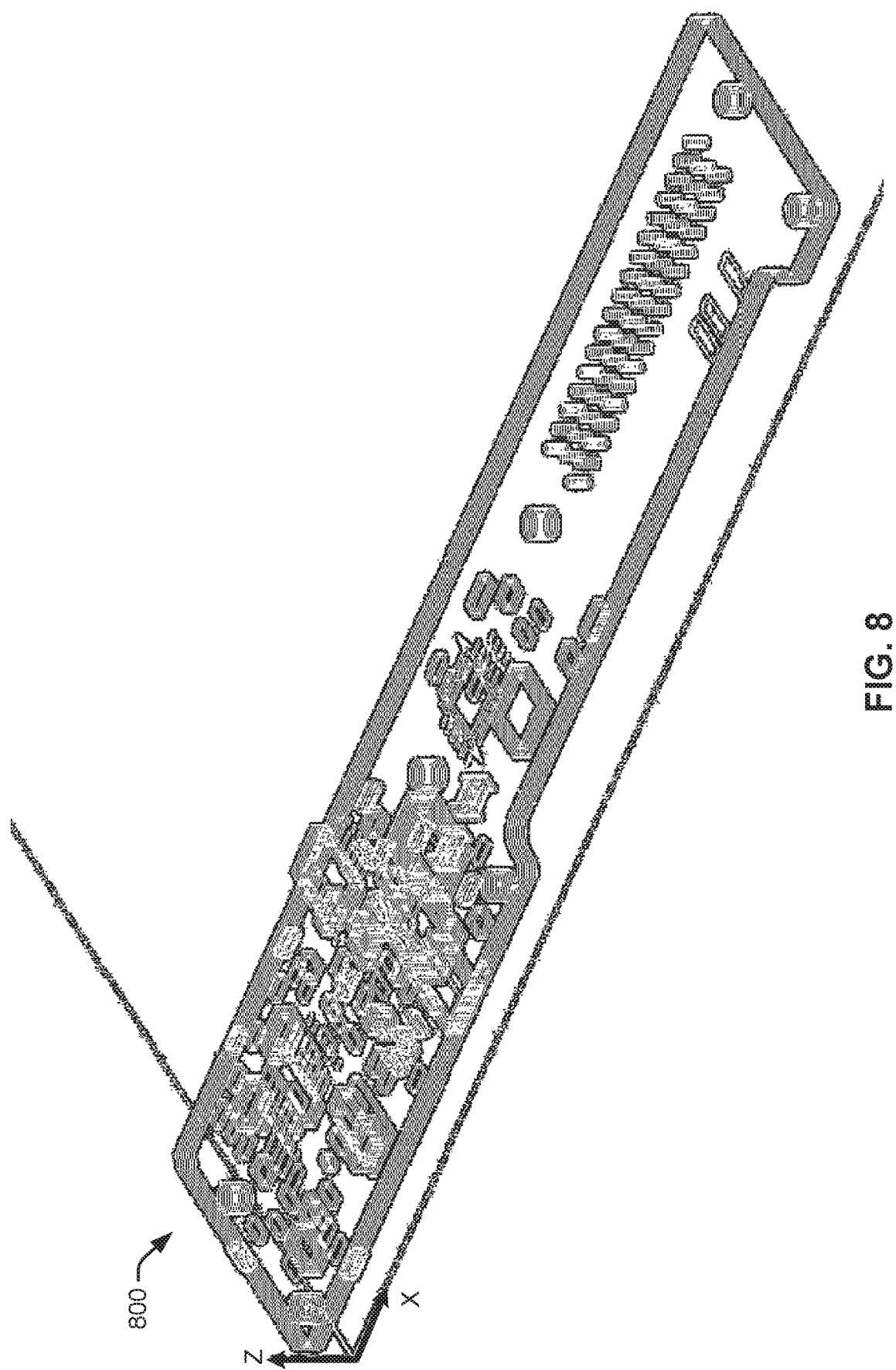
FIG. 8 is a perspective view of the model of FIG. 7, sliced into layers.

This proper orientation is followed by a "Slice" operation. The Slice operation computes part curves by analyzing cross-sections of the STL file. These part curves are created by intersecting the STL model with a series of horizontal planes. Slicing begins at the bottom of the model and progresses sequentially to the top at a constant interval, or slice height. The value of the slice height is based on the material and tip size used in the printer. In the illustrated example, an acrylonitrile butadiene styrene (ABS) material and a tip size compatible with a 0.010 of an inch layer deposit are selected. ABS is a popular thermoplastic used in the industry for rapid prototyping. Other material types may also be used, depending on the application. During printing, material will be added up layer by layer to produce the final product. The resultant STL model 800 sliced with 33 layers, with each layer being 0.010", is shown in FIG. 8.

In the next step of preproduction processing of the model to ready it for printing, support structures are added to the model. Support material is needed underneath nearly the entirety of the area of the model. A "SMART Supports" style can be chosen to minimize the amount of support material used, reduce the build time, and improve support removability for the printed circuit board part. The shape and size of the support region boundary curves are changed from layer to layer to achieve the material and time reductions. The addition of support structures to the model can in some examples be an automated process achieved by software and informed by certain quantitative parameters. That is, the addition of support structures in many cases need not involve human design efforts to manually model the support structures.

Figure 9A:
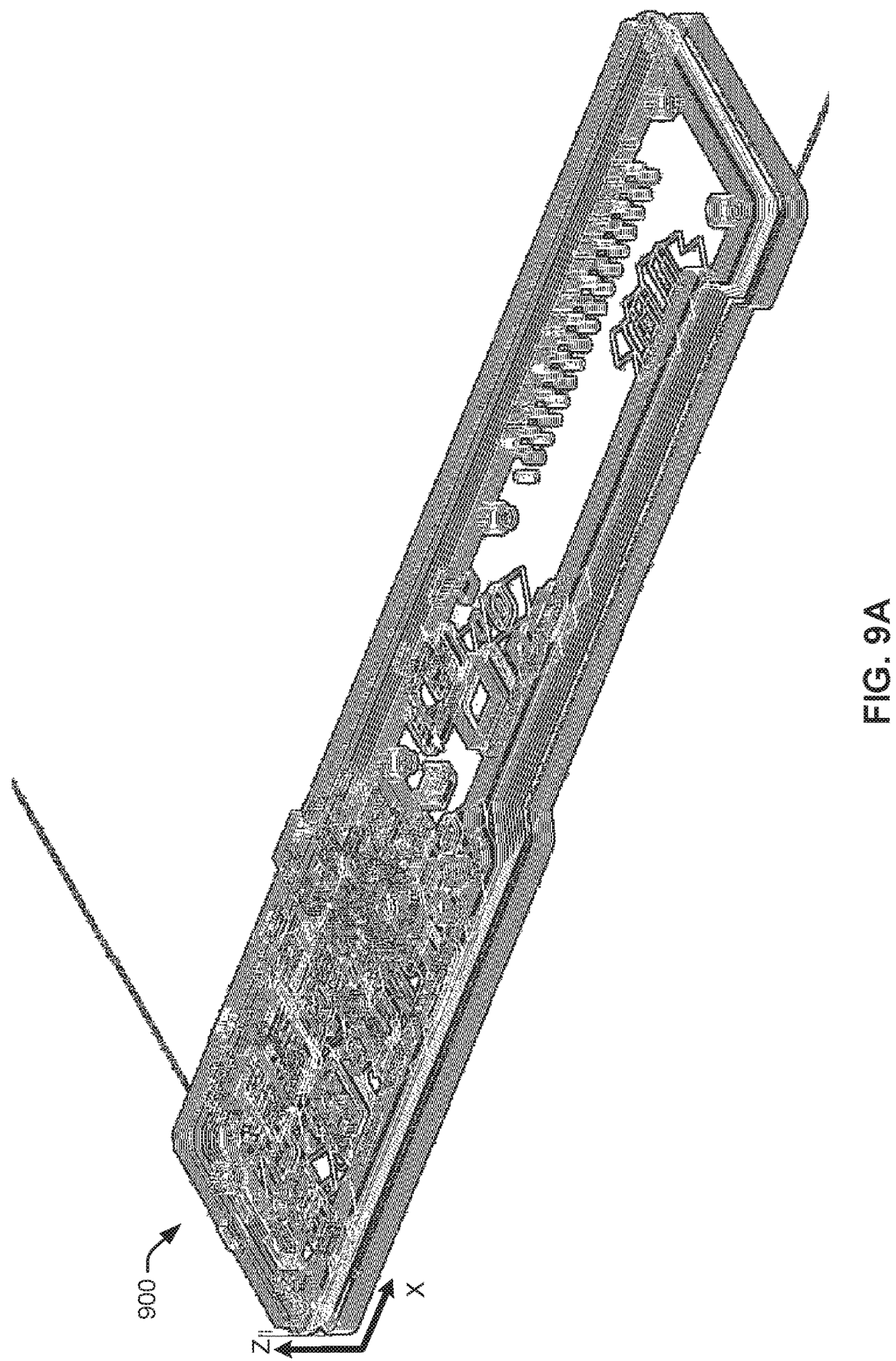
FIGS. 9A-D respectively show perspective and various plan views of the STL model of FIG. 8 with support curves added.
Figure 9B:
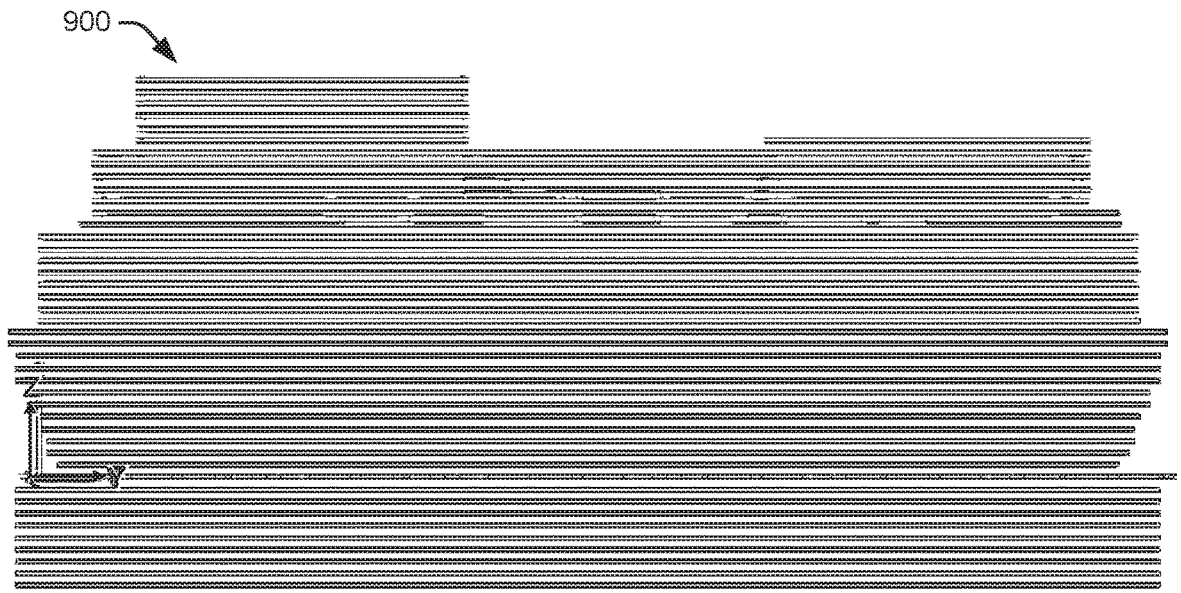
Figure 9C:
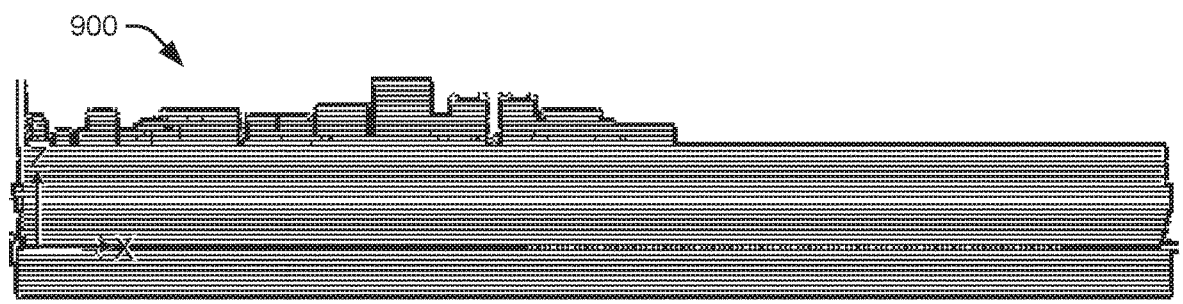
Figure 9D:
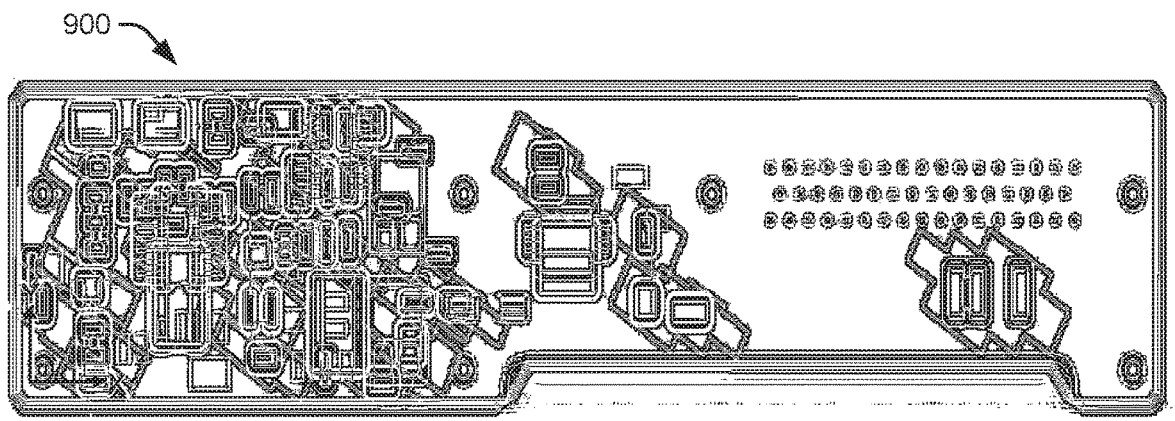
Figure 10:
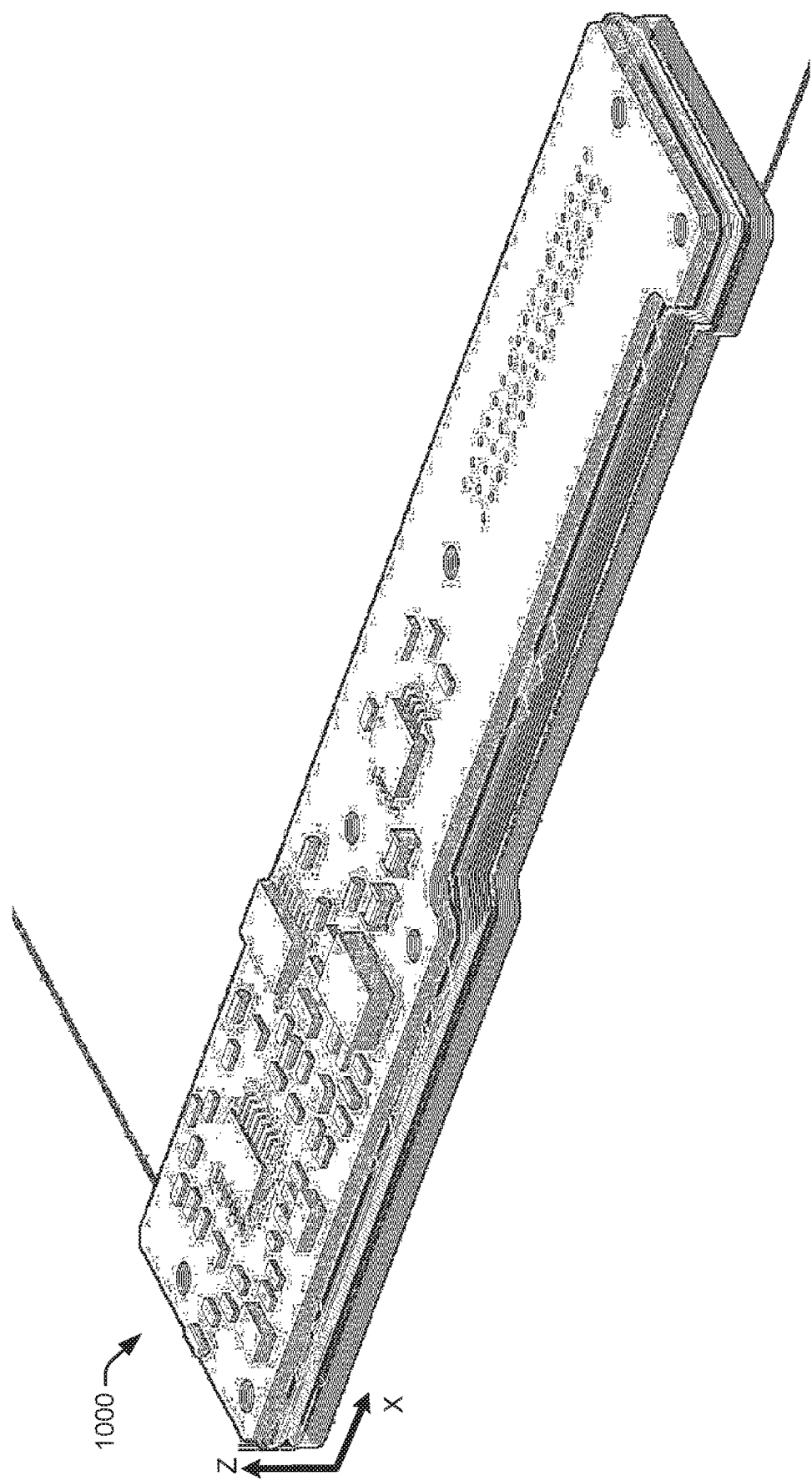
FIG. 10 is perspective view of the model of FIGS. 9A-D, showing the model with support curves.

The printed circuit board part model 900 sliced with support curves is shown in perspective and various plan views in FIGS. 9A-D. These support curves are used to maintain and build angles, hole peripheries, cavities, overhang, hollow attributes, and portions of a model that extend outward. The support curves also prevent the model from sagging or collapsing on itself during the fused-deposition printing process. The resultant support structures will ultimately be disposed of via mechanical or chemical removal. 43 layers are shown in model 900, including foundational and support material layers. FIG. 9A is a three-quarters perspective view of the STL model 900 of the circuit board. FIG. 9B is a right-side plan view of the STL model 900 of the circuit board. FIG. 9C is a front plan view of the STL model 900 of the circuit board. FIG. 9D is a top plan view of the STL model 900 of the circuit board. FIG. 10 illustrates the STL model 1000 with the support curves.

Figure 11:
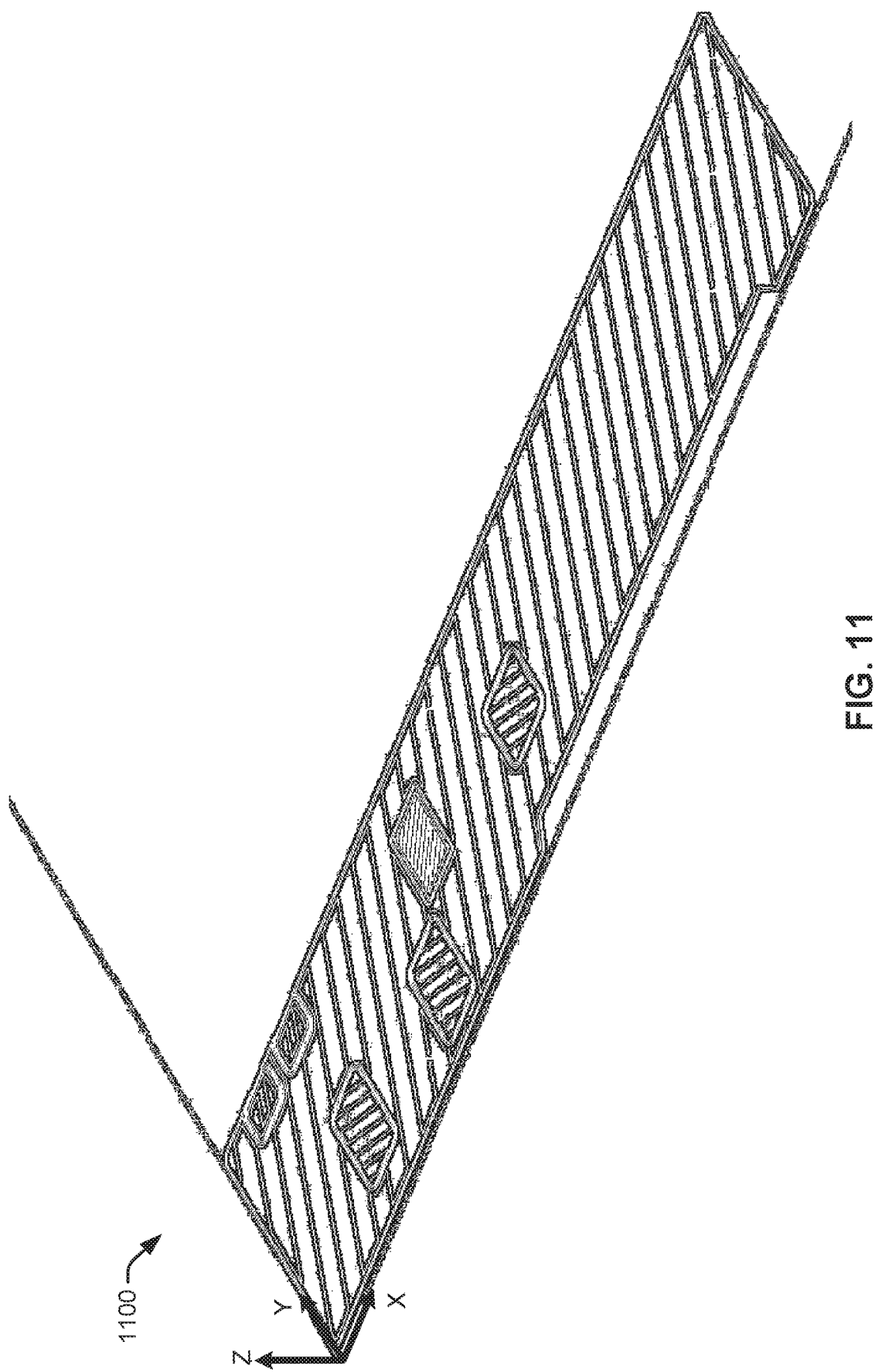
FIG. 11 is a perspective view of a single layer of the model of FIG. 10.

Next, based on the STL file with added support curves, the toolpaths and boundary curves are created to provide detailed positional data and the trajectory for the printer head extrusion tips, to print both the model and its associated support structures. FIG. 11 shows a single layer 1100 of the model of FIG. 10.

In a detailed 3D print such as the one illustrated in FIGS. 5-11, mechanical removal of the support structures (as by manually cutting them away or using manual or automated sawing or grinding tools) may not be achievable due to the high risk of damaging the part involved in such mechanical removal. Accordingly, the printed circuit board part can be immersed in an ultrasonic tank mixture (consisting, for example of a 50%-50% mixture of water and sodium hydroxide (NaOH), e.g., 11 gallons of water with 950 grams of sodium hydroxide) to dissolve the support material by agitating the support material the directed energy of acoustical waves, resulting in the finished integrated circuit board mockup part.

Figure 12:
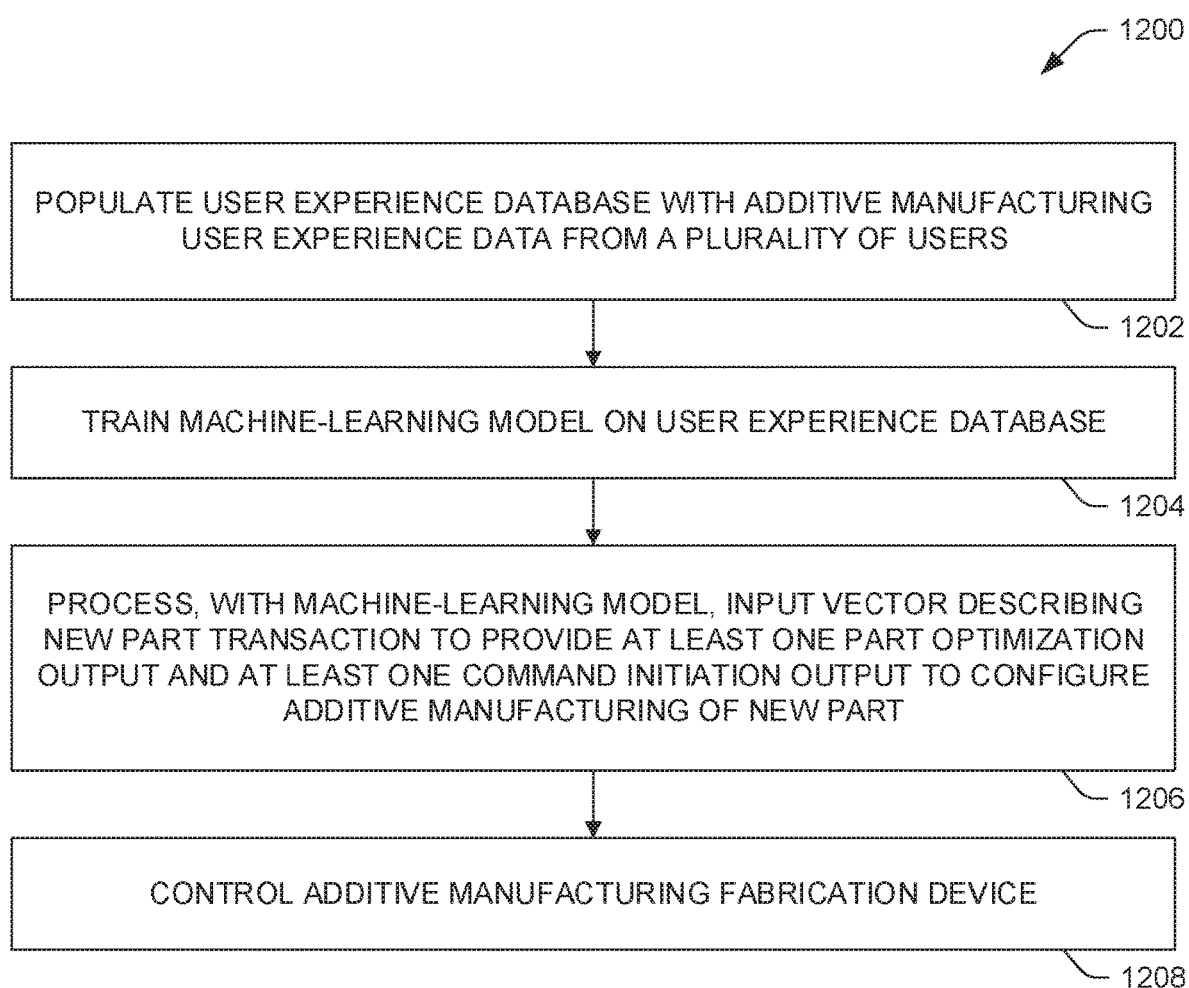
FIG. 12 is a flow diagram of an example method of machine-learning-based additive manufacturing using manufacturing data.

FIG. 12 illustrates a method 1200 for machine-learning based additive manufacturing. A user experience database can be populated 1202 with additive manufacturing user experience data from a plurality of users. For example, the user experience database can consist of a plurality of entries, each entry in the user experience database including at least data defining requirements for an additively manufactured part, specifications describing an additive manufacturing fabrication device, a selection of a raw material type fed to the fabrication device for fabrication of the part, a fabrication spatial orientation of the part within the fabrication device, a fabrication slicing resolution of the part, and toolpaths taken by the device in fabricating the part. For example, each entry in the user experience database is a timestamped block in a blockchain. A machine-learning model (ML model) can be trained 1204 based on the user experience database. Then, the machine-learning model is used to process 1206 an input vector describing a new part transaction, to provide at least one part optimization output and at least one command initiation output to configure additive manufacturing of a new part. As examples, the at least one part optimization output can include a fabrication spatial orientation of the new part, a fabrication slicing resolution of the new part, a set of support curves describing support structures additively manufactured along with the new part, and/or a selection of material type from which the new part is additively manufactured; the at least one command initiation output can include, for example, a command sent to a 3D printer to initiate printing along a toolpath generated by the machine-learning model based on the input vector. An additive manufacturing fabrication device, such as a 3D printer, can then be controlled 1208 based on the command initiation output, e.g., to fabricate the new part on the basis of and in accordance with the ML model outputs. In some examples, a computer-readable medium (or media) can contain instructions that execute to command a computer processor to perform the method 1200.

The machine-learning-based additive manufacturing systems and methods described herein can automatically incorporate lessons learned from previous part builds to prevent the repeating of errors and to enable affordability, reliability, and maintainability in an additive manufacturing production system. The machine learning model of the described systems and methods can also serve as a predictive tool for potential flaws or defects that may occur in the manufacturing process. The incorporation of blockchain technology in the described systems and methods and allows efficient additive manufacturing experience data sharing within a potentially geographically decentralized enterprise or organization, independent of site geography. The present systems and methods can dramatically lower costs on builds for new programs, quickly enable design improvements, and can become a powerful repository of information that is more permanent, more accessible, and more readily and globally utilizable than the personal experience of any individual personnel member or group of personnel members.

What have been described above are examples of the invention. It is, of course, not possible to describe every conceivable combination of components or methodologies for purposes of describing the invention, but one of ordinary skill in the art will recognize that many further combinations and permutations of the invention are possible. Accordingly, the invention is intended to embrace all such alterations, modifications, and variations that fall within the scope of this application, including the appended claims. Additionally, where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on. The term "part" means part or assembly. The term "printer" means 3D printer.

What is claimed is:

1. A machine-learning-based additive manufacturing method comprising:
    processing, with a machine-learning model, an input vector describing a new part transaction to provide at least one part optimization output and at least one command initiation output to configure additive manufacturing of a new part,
        the at least one part optimization output comprising a set of support curves describing support structures to be additively manufactured along with the new part, the support structures being sacrificial structures that support the additive manufacturing of the new part, and that are not components of the new part but that are configured to be removed after additive-manufacturing, the set of support curves reducing the amount of time needed to additively manufacture the part or reducing the amount of time needed to remove the support structures after additive manufacturing, as compared to a different set of support curves,
        the at least one part optimization output further comprising a fabrication spatial orientation of the new part that defines the spatial orientation at which the new part is to be additively manufactured and that reduces the amount of time needed to additively manufacture the part or the amount of material used in the support structures as compared to a different spatial orientation,
        the at least one part optimization output further comprising a fabrication slicing resolution of the new part that defines a resolution at which the new part is to be additively manufactured and that reduces the amount of time needed to additively manufacture the part as compared to a different fabrication slicing resolution; and
    fabricating the new part using additive manufacturing based on the at least one part optimization output and the at least one command initiation output,
    wherein the machine-learning model is trained based on entries in a user experience database, entries in the user experience database each including at least data defining
        requirements for an additively manufactured part previously fabricated or attempted to be fabricated,
        specifications describing an additive manufacturing fabrication device,
        a selection of a raw material type fed to the fabrication device for fabrication of the additively manufactured part,
        a fabrication spatial orientation of the additively manufactured part within the fabrication device,
        a fabrication slicing resolution of the additively manufactured part, and
        a toolpath taken by the fabrication device in fabricating the additively manufactured part,
    wherein the machine-learning model provides the at least one part optimization output including the set of support curves describing the support structures, the fabrication spatial orientation of the new part, and the fabrication slicing resolution of the new part based on the input vector describing the new part transaction and on the entries in the user experience database.

2. The method of claim 1, wherein each entry in the user experience database is a timestamped block in a blockchain.

3. The method of claim 1, wherein the at least one part optimization output comprises a selection of material type from which the new part is additively manufactured.

4. The method of claim 1, wherein the at least one command initiation output comprises a command sent to a 3D printer to initiate printing along a toolpath generated by the machine-learning model based on the input vector.

5. A system for machine-learning-based additive manufacturing, the system comprising:
    a user experience database stored on or distributed across one or more non-transitory computer-readable memories, entries in the user experience database each including at least data defining
        requirements for an additively manufactured part previously fabricated or attempted to be fabricated,
        specifications describing an additive manufacturing fabrication device,
        a selection of a raw material type fed to the fabrication device for fabrication of the additively manufactured part,
        a fabrication spatial orientation of the additively manufactured part within the fabrication device,
        a fabrication slicing resolution of the additively manufactured part, and
        a toolpath taken by the fabrication device in fabricating the additively manufactured part;
    a processor configured to execute instructions implementing a machine-learning model trained based on the entries in the user experience database, the machine-learning model being configured to process an input vector describing a new part transaction to provide at least one part optimization output and at least one command initiation output to configure additive manufacturing of a new part,
        the at least one part optimization output comprising a set of support curves describing support structures to be additively manufactured along with the new part, the support structures being sacrificial structures that support the additive manufacturing of the new part, and that are not components of the new part but that are configured to be removed after additive-manufacturing, the set of support curves reducing the amount of time needed to additively manufacture the part or reducing the amount of time needed to remove the support structures after additive manufacturing, as compared to a different set of support curves,
        the at least one part optimization output further comprising a fabrication spatial orientation of the new part that defines the spatial orientation at which the new part is to be additively manufactured and that reduces the amount of time needed to additively manufacture the part or the amount of material used in the support structures as compared to a different spatial orientation,
    the at least one part optimization output further comprising a fabrication slicing resolution of the new part that defines a resolution at which the new part is to be additively manufactured and that reduces the amount of time needed to additively manufacture the part as compared to a different fabrication slicing resolution,
  wherein the machine-learning model provides the at least one part optimization output including the set of support curves describing the support structures, the fabrication spatial orientation of the new part, and the fabrication slicing resolution of the new part based on the input vector describing the new part transaction and on the entries in the user experience database.

6. The system of claim 5, wherein each entry in the user experience database is a timestamped block in a blockchain.

7. The system of claim 5, wherein the at least one part optimization output comprises a selection of material type from which the new part is additively manufactured.

8. The system of claim 5, wherein the at least one command initiation output comprises a command sent to a 3D printer to initiate printing along a toolpath generated by the machine-learning model based on the input vector.

9. One or more non-transitory computer-readable media storing instructions that when executed by a computer processor, cause the processor to:
  process, with a machine-learning model trained on a user experience database comprising a plurality of entries, an input vector describing a new part transaction to provide at least one part optimization output and at least one command initiation output to configure additive manufacturing of a new part,
  wherein entries in the user experience database each include at least data defining
    requirements for an additively manufactured part previously fabricated or attempted to be fabricated,
    specifications describing an additive manufacturing fabrication device,
    a selection of a raw material type fed to the fabrication device for fabrication of the additively manufactured part,
    a fabrication spatial orientation of the additively manufactured part within the fabrication device,
    a fabrication slicing resolution of the additively manufactured part, and
    a toolpath taken by the fabrication device in fabricating the additively manufactured part,
  wherein the at least one part optimization output comprises a set of support curves describing support structures to be additively manufactured along with the new part, the support structures being sacrificial structures that support the additive manufacturing of the new part, and that are not components of the new part but that are configured to be removed after additive-manufacturing, the set of support curves reducing the amount of time needed to additively manufacture the part or reducing the amount of time needed to remove the support structures after additive manufacturing, as compared to a different set of support curves,
  wherein the at least one part optimization output further comprises a fabrication spatial orientation of the new part that defines the spatial orientation at which the new part is to be additively manufactured and that reduces the amount of time needed to additively manufacture the part or the amount of material used in the support structures as compared to a different spatial orientation,
  wherein the at least one part optimization output further comprises a fabrication slicing resolution of the new part that defines a resolution at which the new part is to be additively manufactured and that reduces the amount of time needed to additively manufacture the part as compared to a different fabrication slicing resolution, and
  wherein the machine-learning model provides the at least one part optimization output including the set of support curves describing the support structures, the fabrication spatial orientation of the new part, and the fabrication slicing resolution of the new part based on the input vector describing the new part transaction and on the entries in the user experience database.

10. The media of claim 9, wherein each entry in the user experience database is a timestamped block in a blockchain.

11. The media of claim 9, wherein the at least one part optimization output comprises a selection of material type from which the new part is additively manufactured.

* * * * *